United States Patent
Krautkramer et al.

(10) Patent No.: US 6,932,929 B2
(45) Date of Patent: Aug. 23, 2005

(54) METHOD OF FORMING COMPOSITE ABSORBENT MEMBERS

(75) Inventors: Patsy A. Krautkramer, Omro, WI (US); Maureen M. Falls, Neenah, WI (US); Robert John Makolin, Neenah, WI (US); Glory Framary Ceman, Appleton, WI (US); William Reeves, Appleton, WI (US); Garry Roland Woltman, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 284 days.

(21) Appl. No.: 10/295,762

(22) Filed: Nov. 15, 2002

(65) Prior Publication Data

US 2003/0150090 A1 Aug. 14, 2003

Related U.S. Application Data

(63) Continuation-in-part of application No. 10/037,438, filed on Dec. 21, 2001, now abandoned.

(51) Int. Cl.⁷ .......................... B29C 47/12; B32B 31/04; B29B 13/00
(52) U.S. Cl. .................. 264/113; 264/177.17; 264/258; 264/271.1; 264/279.1
(58) Field of Search ........................... 264/113, 177.17, 264/258, 271.1, 279.1

(56) References Cited

U.S. PATENT DOCUMENTS 3,339,550 A    9/1967  Haaften
3,793,678 A    2/1974  Appel
3,971,373 A    7/1976  Braun
4,100,324 A    7/1978  Anderson et al.
4,118,531 A   10/1978  Hauser
4,467,012 A    8/1984  Pederson et al.

(Continued)

FOREIGN PATENT DOCUMENTS

EP           0339461 B1    1/1993
WO       WO 9824621 A1    6/1998

OTHER PUBLICATIONS

PCT Search Report, Mar. 21, 2003.

*Primary Examiner*—Stephen J. Lechert, Jr.
(74) *Attorney, Agent, or Firm*—Dority & Manning, P.A.

(57) ABSTRACT

A method for forming a composite absorbent member is provided that includes:
  a) extruding a first fibrous component through a first meltblowing die and intermingling pulp fibers with the first fibrous component to form a first admixture;
  b) extruding a second fibrous component through a second meltblowing die and intermingling pulp fibers with the second fibrous component to form a second admixture; and
  c) codepositing the first and second admixtures on a collecting surface so as to form a composite structure having at least a first layer and a second layer. The second layer has a higher weight percentage of pulp fibers than the first layer, and the average diameter of the pores within the second layer is smaller than the average diameter of the pores within the first layer.

31 Claims, 3 Drawing Sheets

U.S. PATENT DOCUMENTS

| | | |
|---|---|---|
| 4,531,945 A | 7/1985 | Allison |
| 4,604,313 A | 8/1986 | McFarland et al. |
| 4,655,757 A | 4/1987 | McFarland et al. |
| RE32,649 E | 4/1988 | Brandt et al. |
| 4,798,603 A | 1/1989 | Meyer et al. |
| 4,801,494 A | 1/1989 | Datta et al. |
| 4,908,026 A | 3/1990 | Sukiennik et al. |
| 5,145,727 A | 9/1992 | Potts et al. |
| 5,248,309 A | 9/1993 | Serbiak et al. |
| 5,569,226 A | 10/1996 | Cohen et al. |
| 5,609,588 A | 3/1997 | DiPalma et al. |
| 5,643,240 A | 7/1997 | Jackson et al. |
| 5,649,916 A | 7/1997 | DiPalma et al. |
| 5,728,081 A | 3/1998 | Baer et al. |
| 5,834,385 A * | 11/1998 | Blaney et al. ............... 442/382 |
| 5,891,120 A | 4/1999 | Chmielewski |
| 5,916,670 A | 6/1999 | Tan et al. |
| 6,160,197 A | 12/2000 | Lassen et al. |
| 6,323,388 B1 | 11/2001 | Melius et al. |
| 6,387,495 B1 | 5/2002 | Reeves et al. |
| 6,420,626 B1 | 7/2002 | Erspamer et al. |

* cited by examiner

METHOD OF FORMING COMPOSITE ABSORBENT MEMBERS

RELATED APPLICATIONS

The present application is a continuation-in-part of U.S. application Ser. No. 10/037,438, filed on Dec. 21, 2001 abandoned.

BACKGROUND OF THE INVENTION

Absorbent articles (e.g., incontinent devices; sanitary napkins, also referred to as catamenial or feminine pads; pantiliners; pantishields; and the like) are devices often used by a female to absorb the flow of body fluids, such as menses, blood, urine, and other excrements. For instance, absorbent articles sometimes include a liquid-permeable cover, an absorbent core, and a liquid-impermeable baffle. The absorbent core typically contains an airlaid cellulosic tissue disposed adjacent to the baffle that acts as a pad-shaping layer.

However, one problem with many conventional absorbent articles is that they tend to twist and bunch when worn. For instance, as a woman moves, many conventional absorbent articles squeeze between the thighs and result in deformation of the article, thereby causing the upper surface of the article to acquire a curved or convex shape. This twisting and bunching is often referred to as "roping" because a cylindrical profile is imparted to the absorbent article. Roping can cause the absorbent article to absorb less body fluid that contacts its upper surface. Specifically, the fluid discharged from the vagina often runs off the "roped" absorbent article before it can be absorbed, thereby leaking onto the undergarment. This is undesired because it causes discomfort and reduces absorbency.

As such, a need currently exists for an improved absorbent article that can resist bunching and twisting.

SUMMARY OF THE INVENTION

In accordance with one embodiment of the present invention, a method for forming a composite absorbent member is disclosed that comprises forming an absorbent member by a method that includes:

a) extruding a first fibrous component through a first meltblowing die and intermingling pulp fibers with the first fibrous component to form a first admixture;

b) extruding a second fibrous component through a second meltblowing die and intermingling pulp fibers with the second fibrous component to form a second admixture; and c) codepositing the first and second admixtures on a collecting surface so as to form a composite structure having at least a first layer and a second layer. The second layer has a higher weight percentage of pulp fibers than the first layer, and the average diameter of the pores within the second layer is smaller than the average diameter of the pores within the first layer.

In some embodiments, the amount of pulp fibers present within the second layer is at least about 10% by weight greater, and in some embodiments, 25% by weight greater than the amount of pulp fibers present within the first layer. Moreover, the average pore size within the second layer can be at least about 10% smaller, in some embodiments at least about 25% smaller, and in some embodiments, at least about 50% smaller than the average pore size in the first layer. The basis weight of the absorbent member can also vary, such as between about 50 grams per square meter to about 350 grams per square meter, in some embodiments between about 150 grams per square meter to about 250 grams per square meter, and in some embodiments, between about 150 grams per square meter to about 200 grams per square meter. Moreover, in some embodiments, the composite absorbent member can have an Edge Compression value of greater than about 100 grams, in some embodiments between about 150 grams to about 800 grams, and in some embodiments, between about 300 grams to about 600 grams.

In accordance with another embodiment of the present invention, an absorbent article (e.g., incontinent device, sanitary napkin, pantiliner, pantishield, etc.) is disclosed that includes positioning a composite absorbent member between a liquid-permeable cover and a liquid-impermeable baffle. If desired, the absorbent member may be incorporated into an absorbent core that also contains an intake member and/or a transfer delay member. For instance, in one embodiment, the intake member may be positioned adjacent to the liquid-permeable cover and the transfer delay member may be positioned adjacent to the intake member. In such embodiments, the absorbent member may, if desired, be positioned between the transfer delay member and the liquid-impermeable baffle.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
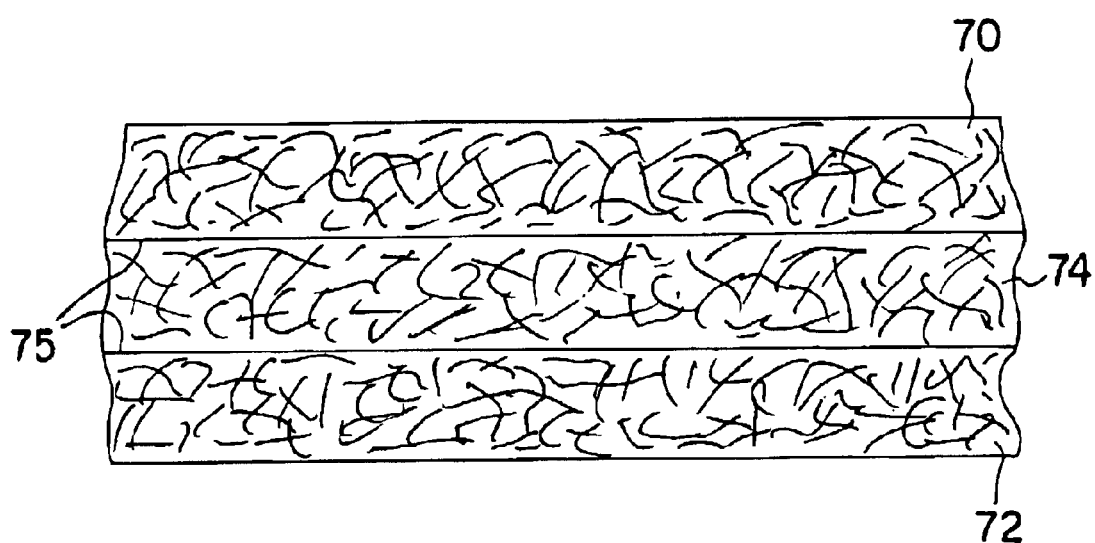
FIG. 1 illustrates a cross-section of one embodiment of a composite absorbent member of the present invention.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

In general, the present invention is directed to a method of forming a composite absorbent member that can be used in or as an absorbent article, such as an incontinent device, sanitary napkin, etc. The composite absorbent member has a controlled pore size distribution within one or more layers to improve the fluid intake rate of the absorbent member and inhibit rewetting. In addition, the composite absorbent member can also be relatively resistant to twisting and bunching. In one embodiment, for example, the composite absorbent member is a coform material formed from three or more layers.

Referring to FIG. 1, for example, one embodiment of a composite absorbent member formed according to the present invention is illustrated. In this embodiment, the absorbent member 22 contains two outer layers 70 and 72 and in inner layer 74 that form a unitary, composite structure. It should be understood, however, that the composite absorbent member 22 can contain any number of layers desired. For example, in one embodiment, the absorbent member 22 can contain four layers. In the illustrated embodiment, each layer contains a mixture of pulp fibers and a synthetic polymer. Typically, it is desired that the outer layers 70 and 72 contain a lesser amount of pulp fibers than the inner layer 74 such that the outer layers 70 and 72 are more hydrophobic than the inner layer 74. Thus, for example, the layer 74 can contain between about 10% to about 90%, in some embodiments from about 20% to about 80%, and in some embodiments, from about 30% to about 70% by weight thermoplastic polymeric fibers. Likewise, the layers 70 and 72 can contain between about 90% to about 10%, in some embodiments between about 80% to about 20%, and in some embodiments, between about 70% to about 30% by weight pulp fibers.

To form a composite material having such a fiber content, any of a variety of processes may be utilized. For instance, in one embodiment, a multi-bank airlaying process may be used. In another embodiment, a "coform" process may be utilized. As used herein, the term "coform" generally refers to continuous melt-spun fibers (e.g., meltblown or spunbond fibers) intermixed with an absorbent material. For example, the melt-spun fibers can be intermixed with staple length fibers, such as described in U.S. Pat. Nos. 4,118,531; 4,100,324 and 4,655,757. Further the melt-spun fibers, in some instances, may be intermixed with superabsorbent particulates, such as described in U.S. Pat. No. 3,971,373. Such superabsorbent materials may be used in combination with the microfibers and staple fibers or in lieu of the staple fibers.

Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Moreover, some suitable absorbent materials that can be used in the coform material include staple fibers, such as polyester, rayon, cotton, pulp fibers, and the like. Pulp fibers are generally obtained from natural sources such as woody and non-woody plants. Woody plants include, for example, deciduous and coniferous trees. Non-woody plants include, for example, cotton, flax, esparto grass, milkweed, straw, jute, and bagasse. In addition, synthetic wood pulp fibers are also available and may be used with the present invention. Wood pulp fibers typically have lengths of about 0.5 to about 10 micrometers and a length-to-maximum width ratio of about 10/1 to about 400/1. A typical cross-section has an irregular width of about 30 micrometers and a thickness of about 5 micrometers.

Figure 2:
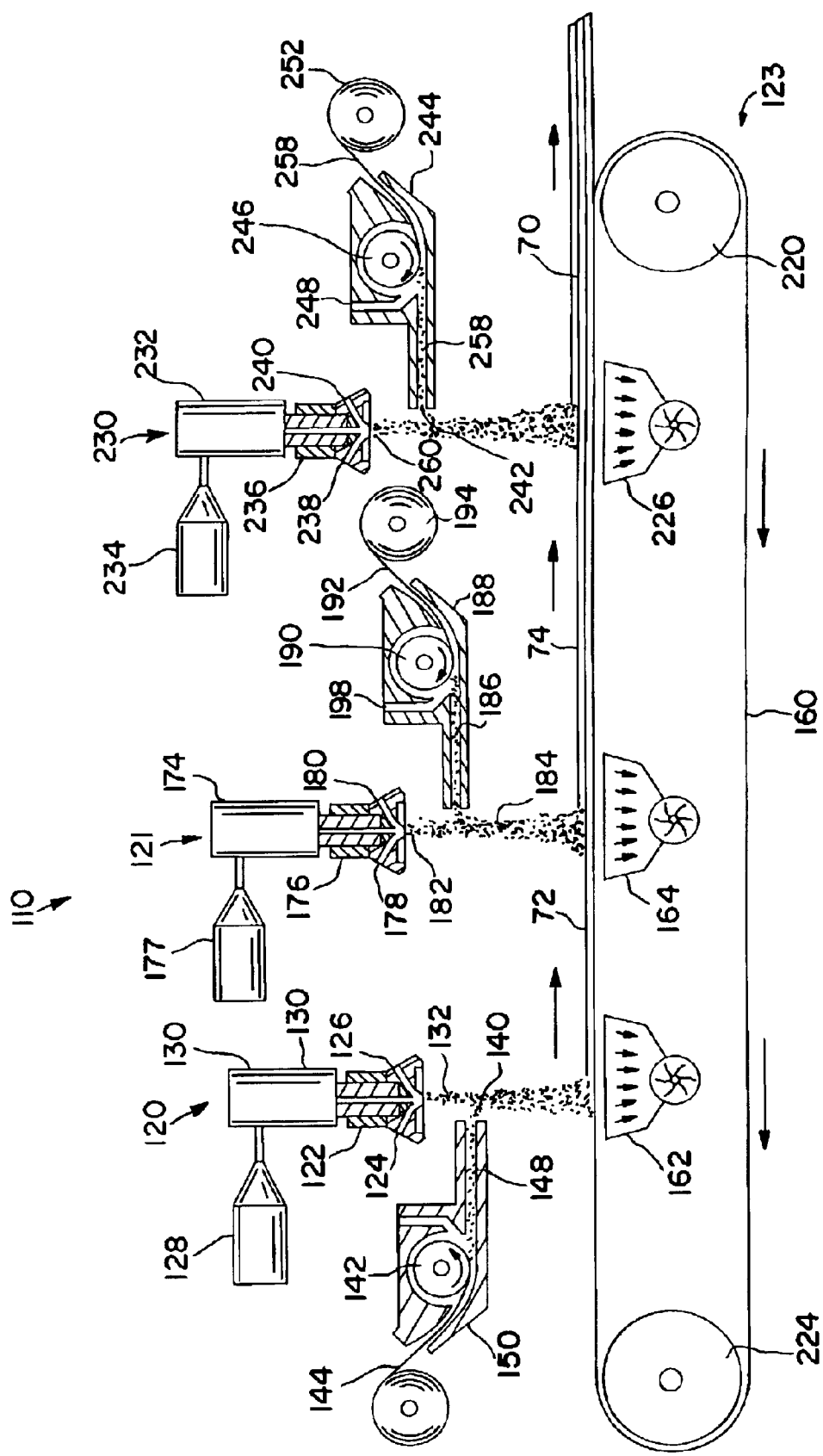
FIG. 2 illustrates one embodiment of a method for forming a composite absorbent member for use in the present invention.

For example, referring to FIG. 2, one embodiment for forming a composite coform material with a differential pulp fiber content is illustrated. As shown, a forming apparatus 110 is composed of three meltblown units 120, 121, and 230, and a movable foraminous belt apparatus 123, such as a wire belt. The meltblown apparatus 120 is composed of a die head 122 through which air streams 124 and 126 pass. A supply device 128 delivers a polymer to an extruder 130 for delivery to the die head 122. The polymer leaves the extruder head 122 and is combined with a primary air stream 132, where the fine polymer streams leaving the die head 122 are attenuated by the converging flows of high velocity heated gas (usually air) supplied through nozzles 124 and 126 to break the polymer streams into discontinuous microfibers of small diameter. The die head 122 typically includes at least one straight row of extrusion apertures.

In general, the resulting microfibers have an average fiber diameter of up to about 10 microns. The average diameter of the microfibers is usually greater than about 1 micron and within the range of about 2 to about 6 microns, often averaging about 5 microns. While the microfibers are predominantly discontinuous, they generally have a length exceeding that normally associated with pulp fibers.

The primary gas stream 132 is merged with a secondary gas stream 140 containing individualized pulp fibers so as to integrate the two different fibrous materials in a single step. The individualized wood pulp fibers typically have a length of about 0.5 to about 10 micrometers and a length to maximum width ratio of about 10:1 to about 400:1. A typical cross-section has an irregular width of about 10 microns and a thickness of about 5 microns. In the illustrated arrangement, the secondary gas stream 140 is formed by a pulp sheet divellicating apparatus, such as described in U.S. Pat. No. 3,793,678 to Appel. This apparatus contains a conventional picker roll 142 having picking teeth for divellicating pulp sheets 144 into individual fibers. The pulp sheets 144 are fed radially along a picker roll radius to the picker roll 142. It is the teeth of the picker roll 142 that allocate the pulp sheets 144 into individual fibers, the resulting separated fibers are conveyed toward the primary air stream 132 through a nozzle or duct 148. A housing 150 covers the picker roll 142. A passageway 152 provides process air to the picker roll in sufficient quantity to provide a medium for conveying the fibers through the forming duct 148 at a velocity approaching that of the picker teeth. The air may be supplied by conventional device, e.g., a blower not shown. Typically, the individual fibers should be conveyed through the duct 148 at substantially the same velocity at which they leave the picker teeth after separation from the pulp sheets 144.

The air stream 132 having pulp fibers from the stream 148 incorporated therein is then placed onto a moving belt 220 that passes beneath the forming die 122 as the microfibers and air stream are directed downwardly. The foraminous belt 160 is provided with suction boxes 162, 164, and 226 driven by blowers that withdraw air from beneath the foraminous belt 220 and provide for uniform laydown of the fibers onto the belt. Two rolls 222 and 224 support the belt 220. While illustrated with three suction devices, the number and size of the suction devices below the belt may be varied.

As illustrated, the meltblowing device 120 lays down a layer of meltblown polymer fibers having pulp fibers entangled therein as layer 72. This passes beneath a second meltblowing device 121 where a second layer 74 is placed thereon and joined to the layer 72.

The layer 74 is formed by the device 121 that is composed of an extruder 174 fed by a material supply device 177. The extruder 174 feeds to a die head 176 that is generally similar to the die head 122, having high velocity air nozzles for supplying air to the extrusion stream 182. As the air streams from the nozzles 178 and 180 merge into the stream 182 and entrain the extruded fibers, they are meltblown into microfibers and mixed with a stream of wood fibers 184, exiting through the nozzle 186 from the picker device 188. In the picker device 188, the picker roll 190 rotates and divellicates pulp sheets 192 as they are unrolled from a supply roll 194. The pulp sheets are divellicated and passed through the nozzle 186 to join the meltblown stream 182. Process air is supplied through the duct 198 of the picker roll housing 188.

As illustrated, the meltblowing device 121 lays down a layer of meltblown polymer fibers having pulp fibers entangled therein as layer 74. This passes beneath a third meltblowing device 230 where a third layer 70 is placed thereon and joined to the layer 74.

The layer 70 is formed by the device 230 that is composed of an extruder 232 fed by a material supply device 234. The extruder 232 feeds to a die head 236 that is generally similar to the die heads 122 and 176, having high velocity air nozzles for supplying air to the extrusion stream 260. As the air streams from the nozzles 240 and 238 merge into the stream 260 and entrain the extruded fibers, they are meltblown into microfibers and mixed with a stream of wood fibers 242, exiting through the nozzle 258 from the picker device 244. In the picker device 244, the picker roll 246 rotates and divellicates pulp sheets 250 as they are unrolled from a supply roll 252. The pulp sheets are divellicated and passed through the nozzle 258 to join the meltblown stream 260. Process air is supplied through the duct 248 of the picker roll housing 244. After leaving the support roller 224, the composite structure of layers 70, 72, and 74 may be further processed by known devices, such as cutters and stackers.

When laid down, the fibers of the layer 74 becomes somewhat entangled with fibers on the surface of the layer 72 and the fibers of the layer 70 become somewhat entangled with fibers on the surface of the layer 74 such that a composite structure is formed. For instance, referring to FIG. 1, one embodiment of a three-layered composite absorbent member is depicted. As shown, the layers 70, 72, and 74 are each composed of an entangled structure of pulp fibers and meltblown polymer fibers that are joined at areas 75. In addition to containing three layers, it should also be understood that the composite material may also contain other layers as well. For example, in one embodiment, a five-layered composite material can be formed in a manner similar to that described above and shown in FIG. 2, except that two additional meltblown units would be utilized. Various methods for forming such composite coform materials are described in U.S. Pat. No. 4,655,757 to McFarland, et al., which is incorporated herein in its entirety by reference thereto for all purposes.

Moreover, in some embodiments, the composite structure can be formed from a process that utilizes a number of meltblown units that is greater or less than the number of equivalent layers. For example, in one embodiment, two meltblown units, such as described above, can be used to form a composite structure containing the equivalent of three layers. In this embodiment, one meltblowing unit can lay down a first layer containing pulp fibers and meltblown fibers. Likewise, the other meltblowing unit also lays down a second layer containing pulp fibers and meltblown fibers. In some instances, the pulp fibers and meltblown fibers tend to segregate such that one surface of the layer contains a greater proportion of pulp fibers than the other surface. Based on the tendency of the fibers to segregate in this manner, the surfaces of each layer having a greater proportion of pulp fibers can be placed adjacent to one another. Thus, the resulting composite structure can have the equivalent of three layers, wherein the inner portion of the structure is the equivalent of a predominantly pulp fiber layer (e.g., layer 74), while the outer portions of the structure are the equivalent of predominantly meltblown fiber layers (e.g., layers 70 and 72).

Regardless of the manner in which the composite structure is formed, by a differential fiber content in each of the layers, such as described above, the composite absorbent member of the present invention can possess a variety of different beneficial properties. For example, as discussed above, the outer layers 70 and 72 can each contain a lesser amount of pulp fibers than the inner layer 74 such that the outer layers 70 and 72 are relatively hydrophobic and the inner layer 74 is relatively hydrophilic. Moreover, by varying the fiber content in each layer, the pore size distribution of the layers can also be readily controlled. Specifically, layers having a relatively large amount of pulp fibers tend to have smaller pore sizes. Although not limited in theory, it is believed that this is the result of a greater level of hydrogen bonding within a layer containing more pulp fibers, thus causing the fibers to be located closer in proximity to each other so that smaller pores are formed. On the other hand, layers having less pulp fibers tend to display less hydrogen bonding, thereby causing larger pores to be formed.

Figure 3:
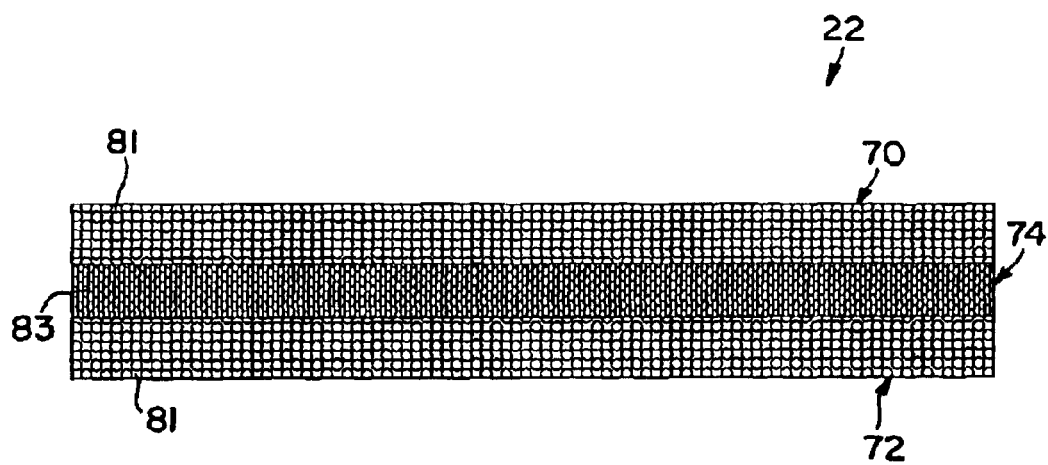
FIG. 3 illustrates a cross-section of a composite absorbent member formed according to one embodiment of the present invention.

Referring to FIG. 3, for example, the outer layers 70 and 72 can have pores 81 that are relatively large in diameter, while the layer 74 can have pores 83 that are relatively small in diameter. In some embodiments, the average pore size within the inner layer 74 is at least about 10% smaller, in some embodiments at least about 25% smaller, and in some embodiments, at least about 50% smaller than the average pore size in the outer layers 70 and 72. Due to the presence of such larger pores, the layer 70 can receive fluids at a relatively fast rate. Moreover, as a result of the hydrophobic nature of the layer 70 and the hydrophilic nature of the layer 74, fluids also tend to flow quickly through the layer 70 and into the inner layer 74. Once present within the inner layer 74, the fluids are absorbed by the hydrophilic pulp fibers. In addition, because fluids do not tend to flow in a direction from smaller pores to larger pores, the fluid absorbed within the inner layer 74 does not readily flow into the outer layer 72 or back into the layer 70, which each have pores that are relatively larger in diameter than the pores of the inner layer 74. This allows the fluid to remain absorbed in the inner layer 74, inhibiting rewetting of the outer surfaces.

To achieve a pore size distribution, such as described above, it is typically desired that each layer of the composite absorbent member have a different pore size distribution than an adjacent layer. In this manner, the composite absorbent member can possess properties that differ from layer to layer. For example, in one embodiment of a three-layered absorbent member, such as shown in FIG. 1, the inner layer 74 typically contains pulp fibers in an amount of at least about 10% by weight greater than adjacent layers 70 and 72, and in some embodiments, at least about 25% by weight greater than adjacent layers 70 and 72. As discussed above, by containing a greater amount of pulp fibers, the inner layer 74 is able to form smaller pores than the outer layers 70 and 72.

Moreover, the outer layers 70 and/or 72 can also contain a certain content of the thermoplastic polymer such that the resulting absorbent article can possess greater strength and stiffness to inhibit bunching and twisting of the article. For example, the Edge-wise Compression (EC) value generally reflects the stiffness of a dry absorbent material. Accordingly, the Edge-wise Compression value can also reflect the ability of the absorbent article to resist twisting and bunching when positioned between the legs of the wearer, and can provide a good indication of desired comfort and fit.

The method by which the Edge-wise Compression (EC) value can be determined is as follows. A piece of the absorbent material (e.g., 2"×12" or 1"×10") is cut with its longer dimension aligned with the longitudinal direction of the product or raw material web. The weight of the sample is determined. The thickness of the material is determined under a 0.2 psi load. The material is formed into a cylinder having a height of 2 inches and, with the two ends having 0 to about 0.125 inch overlap, the material is stapled together with three staples. One staple is near the middle of the width of the product and the other two nearer each edge of the width of the material. The longest dimension of the staple is in the circumference of the formed cylinder to minimize the effect of the staples on the testing.

An "Instron" tensile tester, or other similar instrument, is configured with a bottom platform, a platen larger than the circumference of the sample to be tested and parallel to the bottom platform, attached to a compression load cell placed in the inverted position. The specimen is placed on the platform, under the platen. The platen is brought into contact with the specimen and compresses the sample at a rate of 25 mm/min. The maximum force obtained in compressing the sample to 50% of its width (1 inch) is recorded. If the material buckles, it is typical for the maximum force to be reached before the sample is compressed to 50%.

If the sample has a length smaller than 12 inches (e.g., 1"×10"), certain modifications may be needed. For instance, The Handbook Of Physical And Mechanical Testing Of Paper And Paperboard, Richard E. Mark editor, Dekker 1983, (Vol. 1) provides a detailed discussion of the edgewise compression strength. Based on theoretical models governing buckling stresses, in the Edge-wise Compression configuration described, the buckling stress is proportional to $E*t^2/(H^2)$ with the proportionality constant being a function of $H^2/(R*t)$ where E is the Elastic modulus, H is the height of the cylinder, R is the radius of the cylinder, and t is the thickness of the material. Expressing the stress in terms of force per basis weight, it can be shown that the parameter that needs to be maintained as a constant is $H^2/R$. Therefore, for a sample that is smaller than 12 inches, the largest possible circle should be constructed and its height (width of the sample being cut out) adjusted such that $H^2/R$ equals 2.1 inches. A description of the method for determining Edge-Compression values may also be found in U.S. Pat. No. 6,323,388 to Melius, et al.

In general, the absorbent member 22 has an Edge-Wise Compression (EC) value of at least about 100 grams, in some embodiments between about 150 to about 800 grams, and in some embodiments, between about 300 to about 600 grams. By forming the absorbent member 22 to achieve such an Edge-Wise Compression value, the resulting absorbent article 10 can be flexible enough to provide comfort to a user, yet stiff enough to resist bunching and twisting. The basis weight of the composite absorbent member 22 can also vary, such as from about 50 to about 350 grams per square meters (gsm), in some embodiments from about 150 to about 250 gsm, and in some embodiments, from about 150 to about 200 gsm.

The absorbent member 22 may also contain additional materials to enhance its properties. For example, in some embodiments, one or more layers of the absorbent member 22 may contain a superabsorbent material to enhance absorption capacity. Superabsorbents have the ability to absorb a great amount of fluid in relation to their own weight. Typical superabsorbents used in sanitary napkins can absorb anywhere from about 5 to about 60 times their weight in blood. Superabsorbent materials are produced in a wide variety of forms including, but not limited to, particles, fibers and flakes.

It has been found that superabsorbents having a high mechanical stability in the swollen state, an ability to rapidly absorb fluid, and ones having a strong liquid binding capacity perform well in absorbent articles. Hydroxyfunctional polymers have been found to be good superabsorbents for this application. For example, a hydrogel-forming polymer, such as a partially neutralized cross-linked copolymer of polyacrylic acid and polyvinyl alcohol, can be utilized. After the polymer is formed, it is mixed with about a 1% anhydrous citric acid powder. The citric acid has been found to increase the ability of the superabsorbent to absorb menses and blood. This is particularly beneficial for use in a sanitary napkin or other feminine pads. The finely ground, anhydrous citric acid powder, which is void of water, along with trace amounts of fumed silica, is mixed with the polymer that may have been screened to an appropriate particle size. This mixture may also be formed into a composite or a laminate structure. Such superabsorbents can be obtained from Dow Chemical, Hoechst-Celeanese, and Stockhausen, Inc., among others. This superabsorbent is a partially neutralized salt of cross-linked copolymer of polyacrylic acid and polyvinyl alcohol having an absorbency under load value above about 25.

The superabsorbent typically has a high absorbency under load. That is, it typically has the ability to expand or swell under a restraining pressure, such as about 0.3 psi. The absorbency under load value is a function of gel strength, osmotic pressure within the gel, and the composition of the polymer itself. The absorbency under load value also pertains to the ability of the gel to swell against other superabsorbent particles as well as against adjacent fibers when under pressure. For purposes of this invention, a superabsorbent having a high absorbency under load is defined as having a value of about 20 or higher, and particularly about 25 or higher. Some suitable superabsorbents are taught in U.S. Pat. No. 4,798,603 to Meyers, et al., Re. 32,649 to Brandt, et al. and U.S. Pat. No. 4,467,012 to Pedersen, et al., U.S. Pat. Nos. 4,604,313 and 4,655,757 to McFarland, et al., U.S. Pat. No. 6,387,495 to Reeves, et al., as well as in published European Patent Application 0,339,461 to Kellenberger.

Figure 4:
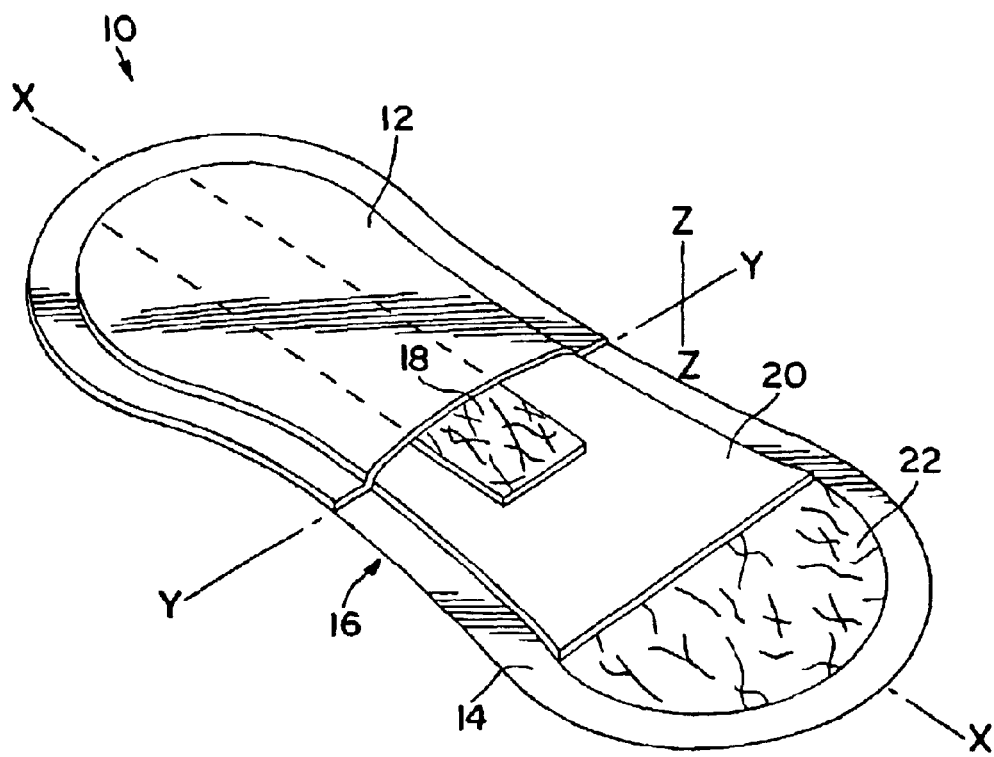
FIG. 4 illustrates a perspective view of an absorbent article formed according to one embodiment of the present invention.

The beneficial properties of the composite member of the present invention can generally be utilized in a wide variety of applications. For instance, referring to FIG. 4, the composite absorbent member 22 can be utilized in an absorbent article 10. For purposes of description only, the absorbent article 10 is illustrated as a sanitary napkin for feminine hygiene having generally a racetrack shape. However, it can be a pantiliner, pantishield, or any other disposable absorbent article that is well known in the art, and can include other shapes, such as oval, hourglass, straight sided, wrapped and peripheral sealed constructions. It should also be noted that absorbent articles come in various sizes and shapes and vary in thickness. For example, in some embodiments, the absorbent article 10 is between about 150 mm to about 320 mm long, and between about 60 mm to about 120 mm wide and has a racetrack shape with rounded ends. Moreover, in some embodiments, the absorbent article has a thickness or caliper of less than about 20 millimeters. For example, when formed as a sanitary napkin, the absorbent article typically has a caliper of less than about 15 millimeters, in some embodiments less than about 5 millimeters, and in some embodiments, less than about 4 millimeters.

In the illustrated embodiment, the absorbent article 10 includes a cover 12, a baffle 14, and an absorbent core 16. The absorbent core 16 is positioned inward from the outer periphery of the absorbent article 10 and includes a body-facing surface positioned adjacent the cover 12 and a garment-facing surface positioned adjacent the baffle 14.

The cover 12 is generally designed to contact the body of the user and is liquid-permeable. The cover 12 can surround the absorbent core 16 so that it completely encases the absorbent article 10. Alternatively, the cover 12 and the baffle 14 can extend beyond the absorbent core 16 and be peripherally joined together, either entirely or partially, using known techniques. Typically, the cover 12 and the baffle 14 are joined by adhesive bonding, ultrasonic bonding, or any other suitable joining method known in the art.

The liquid-permeable cover 12 is sanitary, clean in appearance, and somewhat opaque to hide bodily discharges collected in and absorbed by the absorbent core 16. The cover 12 further exhibits good strike-through and rewet characteristics permitting bodily discharges to rapidly penetrate through the cover 12 to the absorbent core 16, but not allow the body fluid to flow back through the cover 12 to the skin of the wearer. For example, some suitable materials that can be used for the cover 12 include nonwoven materials, perforated thermoplastic films, or combinations thereof. A nonwoven fabric made from polyester, polyethylene, polypropylene, bicomponent, nylon, rayon, or like fibers may be utilized. For instance, a white uniform spunbond material is particularly desirable because the color exhibits good masking properties to hide menses that has passed through it. For instance, U.S. Pat. No. 4,801,494 to Datta, et al. and U.S. Pat. No. 4,908,026 to Sukiennik. et al. teach various cover materials that can be used in the present invention.

If desired, the cover 12 may also be sprayed with a surfactant to enhance liquid penetration to the absorbent core 16. The surfactant is typically non-ionic and should be non-irritating to the skin.

The cover 12 can also contain a plurality of apertures (not shown) formed therethrough to permit body fluid to pass more readily into the absorbent core 16. The apertures can be randomly or uniformly arranged throughout the cover 12, or they can be located only in the narrow longitudinal band or strip arranged along the longitudinal axis X—X of the absorbent article 10. The apertures permit rapid penetration of body fluid down into the absorbent core 16. The size, shape, diameter any number of apertures can be varied to suit one's particular needs.

As stated above, the absorbent article also includes a baffle 14. The baffle 14 is generally liquid-impermeable and designed to face the inner surface, i.e., the crotch portion of an undergarment (not shown). The baffle 14 can permit a passage of air or vapor out of the absorbent article 10, while still blocking the passage of liquids. Any liquid-impermeable material can generally be utilized to form the baffle 14. For example, one suitable material that can be utilized is a microembossed polymeric film, such as polyethylene or polypropylene. In particular embodiments, a polyethylene film is utilized that has a thickness in the range of about 0.2 mils to about 5.0 mils, and particularly between about 0.5 to about 3.0 mils.

As indicated above, the absorbent article 10 also contains an absorbent core 16 positioned between the cover 12 and the baffle 14. In the illustrated embodiment, for example, the absorbent core 16 contains three separate and distinct absorbent members 18, 20 and 22. It should be understood, however, that any number of absorbent members can be utilized in the present invention. For example, in one embodiment, only the absorbent member 22 may be utilized.

As shown, the first absorbent member 18, or intake member, is positioned between the cover 12 and the second absorbent member 20, or transfer delay member. The intake member 18 represents a significant absorbing portion of the absorbent article 10 and has the capability of absorbing at least about 80%, particularly about 90%, and more particularly about 95% of the body fluid deposited onto the absorbent article 10. In terms of amount of body fluid, the intake member 18 can absorb at least about 20 grams, particularly about 25 grams, and more particularly, about 30 or more grams of body fluid.

The intake member 18 can generally have any shape and/or size desired. For example, in one embodiment, the intake member 18 has a rectangular shape, with a length equal to or less than the overall length of the absorbent article 10, and a width less than the width of the absorbent article 10. For example, a length of between about 150 mm to about 300 mm and a width of between about 10 mm to about 40 mm can be utilized. Typically, the intake member 18 is made of a material that is capable of rapidly transferring, in the z-direction, body fluid that is delivered to the cover 12. Because the intake member 18 is generally of a dimension narrower than the absorbent article 10, the sides of the intake member 18 are spaced away from the longitudinal sides of the absorbent article 10 and the body fluid is restricted to the area within the periphery of the intake member 18 before it passes down and is absorbed into the transfer delay member 20. This design enables the body fluid to be combined in the central area of the absorbent article 10 and to be wicked downward.

In general, any of a variety of different materials are capable of being used for the intake member 18 to accomplish the above-mentioned functions. For example, airlaid cellulosic tissues may be suitable for use in the intake member 18. The airlaid cellulosic tissue can have a basis weight ranging from about 10 grams per square meter (gsm) to about 300 gsm, and in some embodiments, between about 100 gsm to about 250 gsm. In one embodiment, the airlaid cellulosic tissue has a basis weight of about 200 gsm. The airlaid tissue can be formed from hardwood and/or softwood fibers. The airlaid tissue has a fine pore structure and provides an excellent wicking capacity, especially for menses. In some embodiments, the intake member 18 may also contain a superabsorbent material, such as described above.

A second absorbent member 20, or transfer delay member, is also positioned vertically below the intake member 18. In some embodiments, the transfer delay member 20 contains a material that is less hydrophilic than the other absorbent members, and may generally be characterized as being substantially hydrophobic. For example, the transfer delay member 20 may be a nonwoven fibrous web composed of a relatively hydrophobic material, such as polypropylene, polyethylene, polyester or the like, and also may be composed of a blend of such materials. One example of a material suitable for the transfer delay member 20 is a spunbond web composed of polypropylene, multi-lobal fibers. Further examples of suitable transfer delay member materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay member 20 are described in U.S. Pat. No. 4,798,603 to Meyer, et al. and U.S. Pat. No. 5,248,309 to Serbiak, et al., which are incorporated herein in their entirety by reference thereto for all purposes. To adjust the performance of the invention, the transfer delay member 20 may also be treated with a selected amount of surfactant to increase its initial wettability.

The transfer delay member 20 can generally have any size, such as a length of about 150 mm to about 300 mm. Typically, the length of the transfer delay member 20 is approximately equal to the length of the absorbent article 10. The transfer delay member 20 can also be equal in width to the intake member 18, but is typically wider. For example, the width of the transfer delay member 20 can be from between about 50 mm to about 75 mm, and particularly about 48 mm.

The transfer delay member 20 of the absorbent core 16 typically has a basis weight less than that of the other absorbent members. For example, the basis weight of the transfer delay member 20 is typically less than about 150 grams per square meter (gsm), and in some embodiments, between about 10 gsm to about 100 gsm. In one particular embodiment, the transfer delay member 20 is formed from a spunbonded web having a basis weight of about 30 gsm.

Besides the above-mentioned members, the absorbent core 16 also includes a composite member 22 formed according to one embodiment of the present invention. For example, the composite member 22 can be a three-layered coform material, such as described above and illustrated in FIG. 1. In this instance, fluids can be wicked from the transfer delay member 20 into the outer layer 70 of the composite absorbent member 20. Because the outer layer 70 is relatively hydrophobic and contains large pores, fluid readily flows therethrough and into the inner layer 74, where it is absorbed by the hydrophilic pulp fibers contained therein. In addition, because the inner layer 74 has smaller pores than the outer layers 70 and 72, the fluid tends to remain in the inner layer 74, thereby inhibiting rewetting. If desired, the composite absorbent member 22 may be formed separately from the intake member 18 and/or transfer delay member 20, or can be formed simultaneously therewith. In one embodiment, for example, the composite absorbent member can be formed on the transfer delay member 20 or intake member 18, which acts a carrier during the coform process described above.

The absorbent article 10 may also contain other components as well. For instance, in some embodiments, the lower surface of the baffle 14 can contain an adhesive for securing the absorbent article 10 to an undergarment. In such instances, a backing (not shown) may be utilized to protect the adhesive side of the absorbent article 10 so that the adhesive remains clean prior to attachment to undergarment. The backing can generally have any desired shape or dimension. For instance, the backing can have a rectangular shape with dimension about 17 to about 21 cm in length and about 6.5 to 10.5 cm in width. The backing is designed to serve as a releasable peel strip to be removed by the user prior to attachment of the absorbent article 10 to the undergarment.

The backing serving as a releasable peel strip can be a white Kraft paper that is coated on one side so that it can be released readily from the adhesive side of the absorbent article 10. The coating can be a silicone coating, such as a silicone polymer commercially available from Akrosil of Menasha, Wis.

Once formed, the absorbent article 10 generally functions to absorb and retain fluids, such as menses, blood, urine, and other excrements discharged by the body during a menstrual period. For example, the intake member 18 can allow the body fluid to be wicked downward in the z-direction and away from the cover 12 so that the cover 12 retains a dry and comfortable feel to the user. Moreover, the intake member 18 can also absorb a significant amount of the fluid. The transfer delay member 20 initially accepts fluid from the intake member 18 and then wicks the fluid along its length and width (-x and -y axis) before releasing the fluid to the composite absorbent member 22. The composite absorbent member 22 then wicks the fluid along its length and width (-x and -y axis) utilizing a greater extent of the absorbent capacity than the transfer delay member 20. Therefore, the composite absorbent member 22 can become completely saturated before the fluid is taken up by the transfer delay member 20. The fluid is also wicked along the length of the transfer delay member 20 and the composite absorbent member 22, thereby keeping the fluid away from the edges of the absorbent article 10. This allows for a greater utilization of the absorbent core 16 and helps reduce the likelihood of side leakage.

In addition to being utilized in an absorbent article in a manner such as described above, the composite member of the present invention may also be utilized in various other ways. For example, referring again to FIG. 4, the composite member of the present invention can function as the absorbent core 16 of the absorbent article 10. In such instances, the outer layer 70 can function in a manner similar to the intake member 18 by absorbing fluids at a relatively fast rate. Likewise, the inner layer 74 can function in a manner similar to the transfer delay member 20 by inhibiting the flow of the fluids into the outer layer 72. In addition, the outer layer 72 can contain a certain amount of thermoplastic polymer so that it enhances the Edge-Compression value of the resulting composite member. In other embodiments, the composite absorbent member of the present invention may constitute the entire absorbent article. For example, in one embodiment, at least one outer layer of the composite absorbent member can be made relatively liquid-impermeable so that it can readily function as the liquid-impermeable baffle described above. Similarly, the composite absorbent member can contain one or more layers to function as the absorbent core and an additional layer that functions as a cover.

Although various embodiments of absorbent articles have been described above, it should be understood that other absorbent article configurations are also contemplated by the present invention. For instance, the materials described above are not required in all instances. Moreover, other materials not specifically discussed herein may also be utilized to form the absorbent article. For example, various configurations of absorbent articles that can be used in the present invention are described in U.S. Pat. No. 6,160,197 to Lassen, et al., U.S. Pat. No. 5,649,916 to DiPalma, et al., U.S. Pat. No. 5,609,588 to DiPalma, et al., and U.S. Pat. No. 5,248,309 to Serbiak, et al., which are incorporated herein in their entirety by reference thereto for all purposes.

The present invention may be better understood with reference to the following example.

EXAMPLE

The ability to form a composite absorbent member in accordance with the present invention was demonstrated. In particular, a two-layered, composite coform material was formed according to the general procedures substantially described above and illustrated in FIG. 2, except that only 2 meltblown units were utilized. For instance, polypropylene resin (PD 701—Hercules) was initially extruded from a series of orifices. The extrusion rate was at about 9 pounds per inch per hour from each of the two (2) meltblown units. The extrusion was at a final temperature of about 500° F. and fibers were attenuated in primary air streams flowing at a sonic velocity and a combined rate of about 325 SCFM at a temperature of about 510° F.

The secondary air stream containing suspended pulp fluff was comprised of Southern pine bleached kraft. The pulp was picked and forced into a fiber jet approximately 2 inches from the primary air stream and 1.5 inches below the die tip. The velocity of the primary air was between about 2 times the velocity of the secondary stream at the point it was introduced. The composite coform material was collected on a wire mesh belt, which was about 10 inches below the extrusion die tip. For the samples below, the speed of the wire mesh belt was varied from between about 160 feet per minute (fpm) to about 330 fpm.

The first meltblown unit in which pulp fibers were added was placed downstream from the second meltblown unit. The two meltblown units were essentially identical, except that each were supplied with differing pulp fiber contents as set forth below in Tables 1–2.

For samples 9–10, a spunbond transfer delay member (0.4 osy) was used as a carrier for the absorbent member, while for samples 11–12, a spunbond transfer delay member (0.8 osy) as a carrier for the absorbent member.

The properties of the samples are set forth below in Tables 1–2.

TABLE 1

Sample Properties

| | Bank 1 | | Bank 2 | | | | |
|---|---|---|---|---|---|---|---|
| Sample | Polymer (wt. %) | Pulp (wt. %) | Polymer (wt. %) | Pulp (wt. %) | Basis Wt. (gsm) | Thickness (mm) | Density (g/cc) |
| 1 | 50 | 50 | 50 | 50 | 162.4274 | 1.9067 | 0.0856 |
| 2 | 40 | 60 | 60 | 40 | 169.8545 | 2.1500 | 0.0793 |
| 3 | 30 | 70 | 70 | 30 | 168.9934 | 2.2950 | 0.0738 |
| 4 | 20 | 80 | 80 | 20 | 171.4691 | 2.2300 | 0.0771 |
| 5 | 40 | 60 | 70 | 30 | 172.2226 | 2.1267 | 0.0811 |
| 6 | 40 | 60 | 80 | 20 | 178.0351 | 2.1600 | 0.0826 |
| 7 | 30 | 70 | 40 | 60 | 160.7052 | 2.1850 | 0.0737 |
| 8 | 30 | 70 | 80 | 20 | 163.2885 | 2.0783 | 0.0788 |
| 9 | 40 | 60 | 40 | 60 | 185.6775 | 1.9567 | 0.0950 |
| 10 | 60 | 40 | 30 | 70 | 185.8927 | 2.0033 | 0.0930 |
| 11 | 40 | 60 | 40 | 60 | 200.9622 | 2.1000 | 0.0957 |
| 12 | 60 | 40 | 30 | 70 | 202.4692 | 2.2033 | 0.0921 |
| 13 | 40 | 60 | 70 | 30 | 161.8892 | 2.1100 | 0.0768 |
| 14 | 40 | 60 | 80 | 20 | 172.5455 | 2.1200 | 0.0814 |

TABLE 2

Sample Properties

| | Bank 1 | | Bank 2 | | | | |
|---|---|---|---|---|---|---|---|
| Sample | Polymer (wt. %) | Pulp (wt. %) | Polymer (wt. %) | Pulp (wt. %) | Basis Wt. (gsm) | Thickness (mm) | Density (g/cc) |
| 15 | 40 | 60 | 40 | 60 | 164.2573 | 2.0317 | 0.0810 |
| 16 | 35 | 65 | 35 | 65 | 163.8267 | 2.1317 | 0.0771 |
| 17 | 30 | 70 | 30 | 70 | 158.6600 | 2.1750 | 0.0731 |

Once the composite coform material was formed, various properties of the resulting absorbent members were tested. In particular, the Edge-Compression (EC) value of a 2"×12" specimen of the material was determined as substantially described above, except that a manual instrument was used to determine the buckling weight instead an Instron tensile tester. Specifically, the manual instrument contained two (2) plexiglass platens having a size larger than the sample. The sample was prepared as described above and placed between the platens. Calibrated weights were then placed on the top platen until the sample collapsed. The weight required to collapse the sample was recorded.

Moreover, the penetration (intake) rate and MD tensile strength of the absorbent members were determined as follows:

Penetration (Intake) Rate: To measure how quickly the coform material would accept a liquid, a penetration rate test was performed using "Z-Date," a synthetic menstrual fluid formulation available from PPG Industries, Inc. of Pittsburgh, Pa. that contains, on a weight percent basis, approximately 82.5% water, 15.8% polyvinyl pyrrolidone and 1.7% salts, coloring agents and surfactants. "Z-Date" has a viscosity of 17 centipoise and a surface tension of 53.5 dynes per centimeter. To determine the penetration rate, a 3"×7" sample of the absorbent member was initially applied with 4 mL of the synthetic menstrual fluid, which was delivered from a fluid reservoir having a 2"×0.5" delivery slot. The time to absorb 4 mL of fluid was then measured in seconds. A lower absorption time as measured in seconds was an indication of a faster intake rate for the particular material. The test was run at conditions of 73.4°+/−3.6° F. and 50% +/−5% relative humidity. Such a procedure is also described in U.S. Pat. No. 5,643,240 to Jackson, et al., which is incorporated herein in its entirety by reference thereto for all purposes.

MD Tensile Strength

MD (machine direction) tensile strength was determined using a MTS/Sintech tensile tester (available from the MTS Systems Corp., Eden Prairie, Minn.). Samples measuring 3 inch wide were cut in the machine direction. For each test, a sample strip was placed in the jaws of the tester, set at a 4 inch gauge length for facial tissue and 2 inch gauge length for bath tissue. The crosshead speed during the test was 10 inches per minute. The tester was connected with a computer loaded with data acquisition system; e.g., MTS TestWork for windows software. Readings were taken directly from a computer screen readout at the point of rupture to obtain the MD tensile strength of an individual sample.

The results are given below in Table 3.

TABLE 3

Sample Results

| Sample | EC (g) | Penetration Rate (s) | MD Tensile (g) |
|---|---|---|---|
| 1 | 369.23 | 23.667 | 1997.10 |
| 2 | 421.55 | 37.500 | 2001.18 |
| 3 | 436.55 | 22.000 | 2451.13 |
| 4 | 399.22 | 19.167 | 2431.93 |
| 5 | 534.57 | 22.667 | 2618.33 |
| 6 | 698.47 | 37.667 | 3268.18 |
| 7 | 380.82 | 14.833 | 1653.27 |
| 8 | 416.83 | 25.333 | 2496.22 |
| 9 | 378.60 | 20.500 | 4346.78 |
| 10 | 375.21 | 20.500 | 4721.72 |
| 11 | 355.34 | 21.000 | 5135.52 |
| 12 | 415.04 | 37.167 | N/A |
| 13 | 544.82 | 37.167 | N/A |
| 14 | 498.07 | 46.667 | N/A |
| 15 | 284.26 | 14.167 | 1491.88 |
| 16 | 178.20 | 19.833 | 1188.14 |
| 17 | 137.00 | 18.333 | 994.28 |

For comparative purposes, an airlaid cellulosic tissue was formed having a basis weight of 175 gsm, a caliper of 2.19 mm, and a density of 0.08 g/cc. The EC value, penetration rate, and MD Tensile strength of the airlaid tissue was tested as described above. The results are given below in Table 4.

TABLE 4

Control Sample Results

| Sample | EC (g) | Penetration Rate (s) | MD Tensile (g) |
|---|---|---|---|
| 18 | 450.73 | 75.167 | 1958.47 |

Thus, as demonstrated above, a composite absorbent member formed according to the present invention can have good absorption characteristics, while also maintaining a relatively high Edge-Compression (EC) value. For instance, the control sample had an EC value of 450.73 grams, while absorbent members formed according to the present invention had EC values up to 698.47 grams while still maintaining a good intake rate. Such high EC values reflect the ability of absorbent members of the present invention, even when used in thin absorbent articles, to inhibit bunching and twisting.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of forming a composite absorbent member, said method comprising:
    a) extruding a first fibrous component through a first meltblowing die and intermingling pulp fibers with said first fibrous component to form a first admixture;
    b) extruding a second fibrous component through a second meltblowing die and intermingling pulp fibers with said second fibrous component to form a second admixture; and
    c) codepositing said first and second admixtures on a collecting surface so as to form a composite structure having at least a first layer and a second layer, wherein said second layer has a higher weight percentage of pulp fibers than said first layer, and wherein the average diameter of the pores within said second layer is smaller than the average diameter of the pores within said first layer.

2. A method as defined in claim 1, wherein the weight percentage of pulp fibers within said second layer is at least about 10% greater than the weight percentage of pulp fibers present within said first layer.

3. A method as defined in claim 1, wherein the weight percentage of pulp fibers within said second layer is at least about 25% greater than the weight percentage of pulp fibers present within said first layer.

4. A method as defined in claim 1, wherein the average pore size within said second layer is at least about 10% smaller than the average pore size within said first layer.

5. A method as defined in claim 1, wherein the average pore size within said second layer is at least about 25% smaller than the average pore size within said first layer.

6. A method as defined in claim 1, wherein the average pore size within said second layer is at least about 50% smaller than the average pore size within said first layer.

7. A method as defined in claim 1, wherein the composite absorbent member has an Edge Compression value of greater than about 100 grams.

8. A method as defined in claim 1, wherein the composite absorbent member has an Edge Compression value of between about 150 grams to about 800 grams.

9. A method as defined in claim 1, wherein the composite absorbent member has an Edge Compression value of between about 300 grams to about 600 grams.

10. A method as defined in claim 1, wherein the basis weight of said composite absorbent member is from about 150 grams per square meter to about 250 grams per square meter.

11. A method as defined in claim 1, wherein the basis weight of said composite absorbent member is from about 150 grams per square meter to about 200 grams per square meter.

12. A method as defined in claim 1, wherein the codepositing of said first and second admixtures forms a composite structure having two layers.

13. A method as defined in claim 1, wherein the codepositing of said first and second admixtures forms a composite structure having three layers.

14. A method as defined in claim 13, wherein the formation of said three layers is accomplished using two meltblown units.

15. A method as defined in claim 1, wherein said first layer, said second layer, or combinations thereof, further comprises a superabsorbent material.

16. A method of forming an absorbent article, said method comprising:
   a) forming an absorbent member by a method that includes:
      i) extruding a first fibrous component through a first meltblowing die and intermingling pulp fibers with said first fibrous component to form a first admixture;
      ii) extruding a second fibrous component through a second meltblowing die and intermingling pulp fibers with said second fibrous component to form a second admixture; and
      iii) codepositing said first and second admixtures on a collecting surface so as to form a composite structure having at least a first layer and a second layer, wherein the weight percentage of pulp fibers in said second layer is at least about 10% greater than the weight percentage of pulp fibers within said first layer, and wherein the average diameter of the pores within said second layer is smaller than the average diameter of the pores within said first layer; and
   b) positioning said absorbent member between a liquid-permeable cover and a liquid-impermeable baffle.

17. A method as defined in claim 16, wherein the weight percentage of pulp fibers within said second layer is at least about 25% greater than the weight percentage of pulp fibers present within said first layer.

18. A method as defined in claim 16, wherein the average pore size within said second layer is at least about 25% smaller than the average pore size within said first layer.

19. A method as defined in claim 16, wherein the average pore size within said second layer is at least about 50% smaller than the average pore size within said first layer.

20. A method as defined in claim 16, wherein the composite absorbent member has an Edge Compression value of greater than about 100 grams.

21. A method as defined in claim 16, wherein the composite absorbent member has an Edge Compression value of between about 150 grams to about 800 grams.

22. A method as defined in claim 16, further comprising positioning an intake member adjacent to said liquid-permeable cover.

23. A method as defined in claim 22, further comprising positioning a transfer delay member adjacent to said intake member.

24. A method as defined in claim 23, wherein said composite absorbent member is positioned between said transfer delay member and said liquid-impermeable baffle.

25. A method as defined in claim 16, wherein the absorbent article has a caliper less than about 15 millimeters.

26. A method as defined in claim 16, wherein the absorbent article has a caliper less than about 5 millimeters.

27. A method of forming a composite absorbent member, said method comprising:
   a) extruding a first fibrous component through a first meltblowing die and intermingling pulp fibers with said first fibrous component to form a first admixture;
   b) extruding a second fibrous component through a second meltblowing die and intermingling pulp fibers with said second fibrous component to form a second admixture;
   c) codepositing said first and second admixtures on a collecting surface so as to form a composite structure having a lower outer layer, an inner layer, and an upper outer layer, wherein the weight percentage of pulp fibers within said inner layer is at least about 10% greater than the weight percentage of pulp fibers within said lower outer layer and said upper outer layer, and wherein the average diameter of the pores within said inner layer is smaller than the average diameter of the pores within said lower outer layer and said upper outer layer.

28. A method as defined in claim 27, wherein the weight percentage of pulp fibers within said inner layer is at least about 25% greater than the weight percentage of pulp fibers present within said lower outer layer and said upper outer layer.

29. A method as defined in claim 27, wherein the average pore size within said inner layer is at least about 10% smaller than the average pore size within said first outer layer and said second outer layer.

30. A method as defined in claim 27, wherein the average pore size within said inner layer is at least about 25% smaller than the average pore size within said first outer layer and said second outer layer.

31. A method as defined in claim 27, wherein the average pore size within said inner layer is at least about 50% smaller than the average pore size within said first outer layer and said second outer layer.

* * * * *